(12) United States Patent
White

(10) Patent No.: US 12,310,767 B1
(45) Date of Patent: May 27, 2025

(54) LEG SUPPORT TOOL FACILITATING X-RAY IMAGING

(71) Applicant: Jonathan D. White, Redding, CA (US)

(72) Inventor: Jonathan D. White, Redding, CA (US)

(*) Notice: Subject to any disclaimer, the term of this patent is extended or adjusted under 35 U.S.C. 154(b) by 232 days.

(21) Appl. No.: 17/839,846

(22) Filed: Jun. 14, 2022

Related U.S. Application Data

(60) Provisional application No. 63/211,674, filed on Jun. 17, 2021.

(51) Int. Cl.
*A61B 6/04* (2006.01)

(52) U.S. Cl.
CPC .................................. *A61B 6/0428* (2013.01)

(58) Field of Classification Search
CPC ...................................................... A61B 6/0428
USPC ...................................... 248/157, 118, 118.3
See application file for complete search history.

(56) References Cited

U.S. PATENT DOCUMENTS

| | | | | |
|---|---|---|---|---|
| 2,119,325 | A * | 5/1938 | Goodhart | A61M 5/52 248/118 |
| 9,579,243 | B2 * | 2/2017 | Rice | A61G 1/003 |
| 10,172,468 | B2 * | 1/2019 | Houghson | F16M 11/28 |
| 10,457,528 | B2 * | 10/2019 | Grant | F16M 11/18 |
| 10,806,650 | B2 * | 10/2020 | Di Lauro | A61M 5/52 |
| 11,259,640 | B2 * | 3/2022 | Tozeski | A61B 5/022 |
| 2015/0351707 | A1 * | 12/2015 | Sampognaro | A61B 6/0428 128/877 |

* cited by examiner

*Primary Examiner* — Todd M Epps
(74) *Attorney, Agent, or Firm* — Heisler & Associates

(57) ABSTRACT

A riser extends up from a base. The base defines a lower portion of the support tool and includes at least one leg extending away from the riser laterally to provide stability to the support tool. An arm also extends away from the riser at a location above the base, with the arm inboard of lateral edges of a footprint of the base. The arm supports a cradle on a portion of the arm spaced from the riser. This cradle includes a saddle open from above which can receive and support bodily extremities such as a leg or arm of a patient. The cradle is preferably formed of radiolucent material to be substantially invisible within medical images of the extremity. Tilt and pivot mechanisms allow the cradle to be pivoted about a vertical axis and tilted about a horizontal axis for optimal positioning of the extremity of the patient.

19 Claims, 4 Drawing Sheets

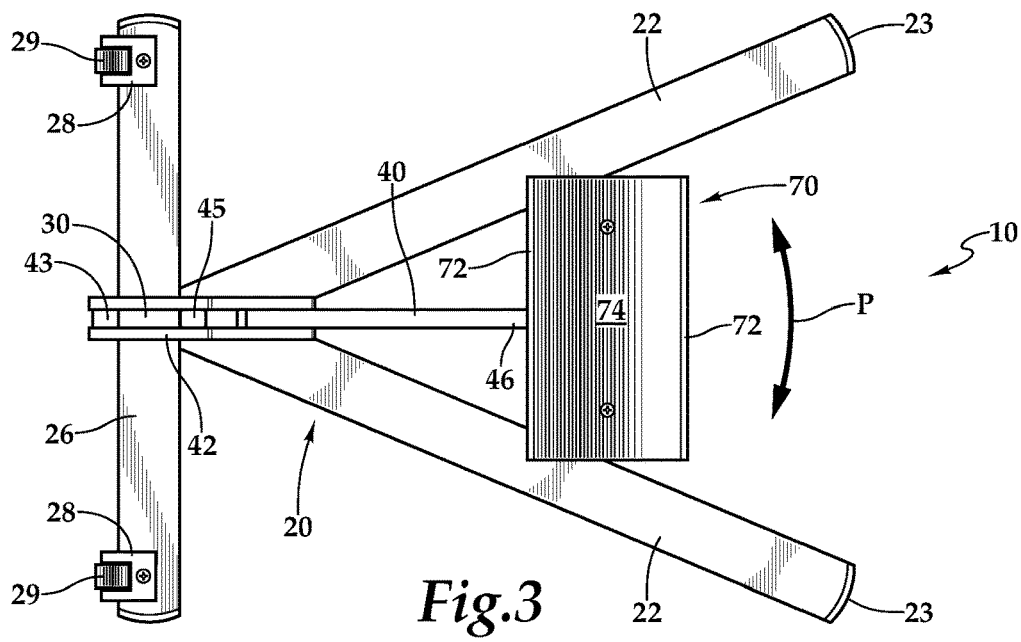
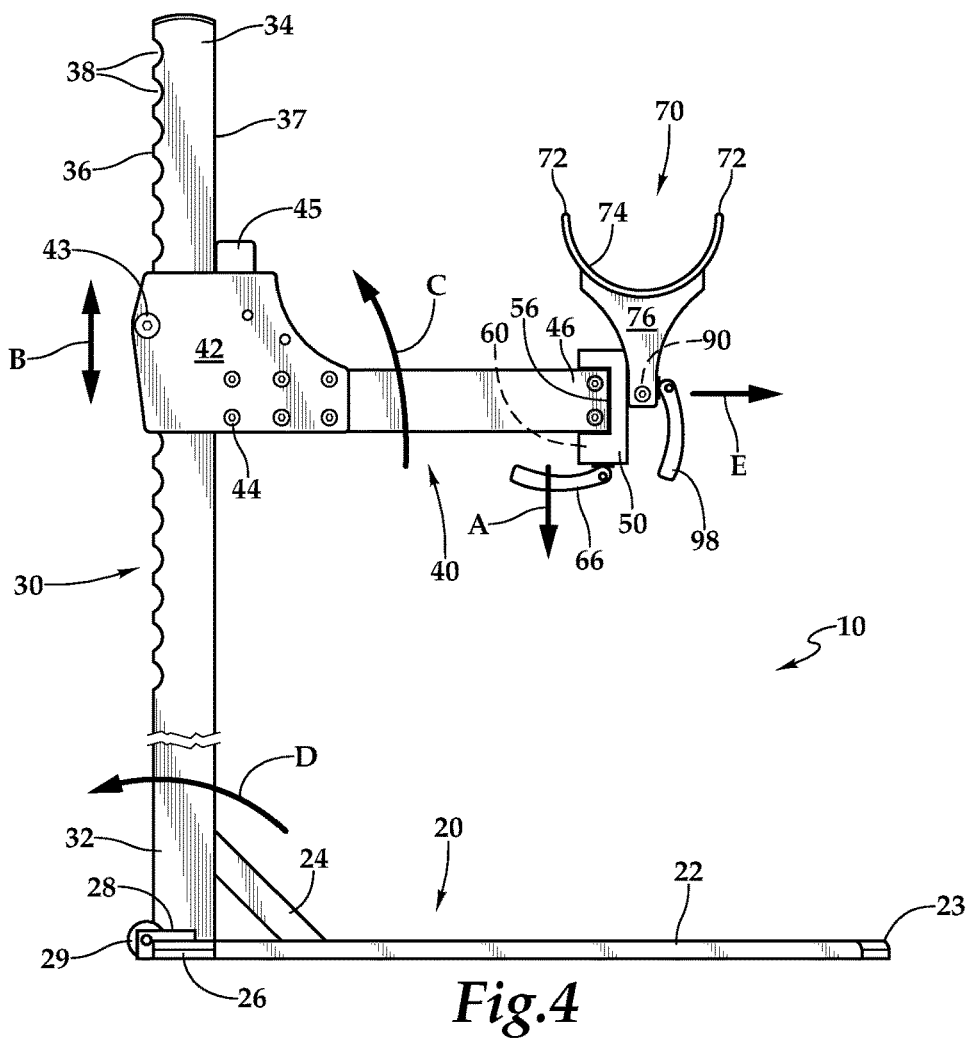

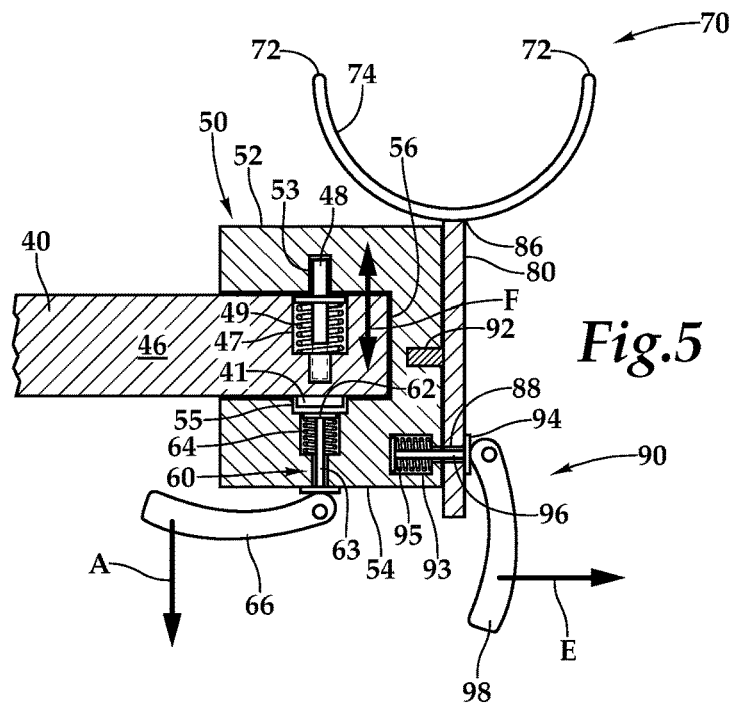
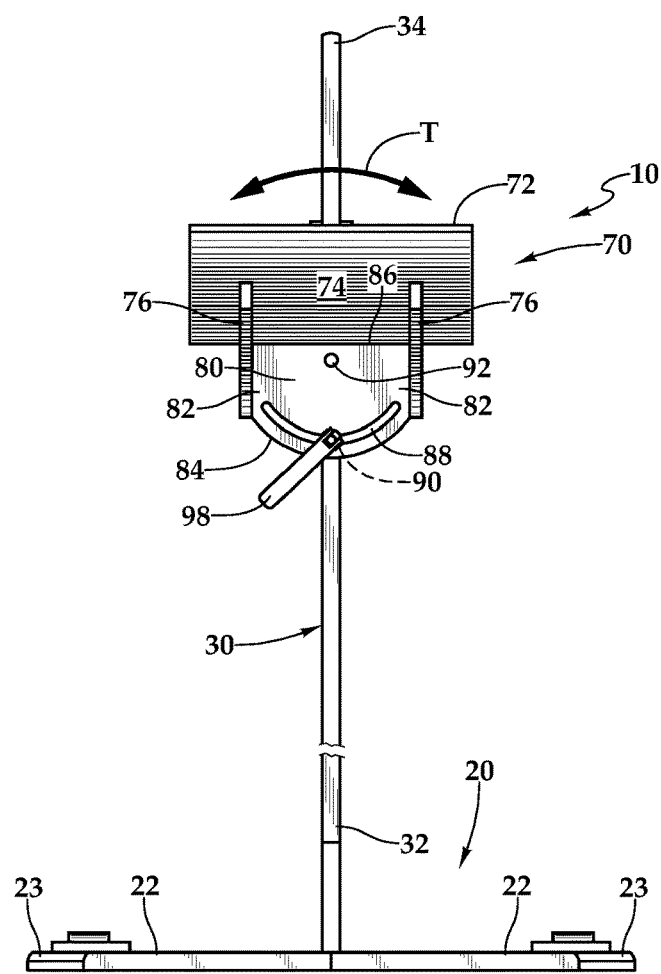
Fig.5
Fig.6

LEG SUPPORT TOOL FACILITATING X-RAY IMAGING

CROSS-REFERENCE TO RELATED APPLICATIONS

This application claims benefit under Title 35. United States Code § 119(e) of U.S. Provisional Application No. 63/211,674 filed on Jun. 17, 2021.

FIELD OF THE INVENTION

The following invention relates to supports for holding body extremities above ground, such as during imaging procedures. More specifically, this invention relates to body extremity supports which are adjustable in height and orientation and which work with a patient while lying in a bed.

BACKGROUND OF THE INVENTION

When imaging different portions of the human body, such as with x-rays, difficulties are often presented in positioning patient anatomy appropriately. Even when a patient is generally healthy and pain-free, ideal imaging equipment orientation and anatomical posture of the patient can be difficult to achieve. When considering that imaging is typically required when a patient has had a traumatic injury or other condition which compromises anatomical mobility and/or amplifies pain associated with anatomical mobility, the difficulties in achieving ideal anatomical posture when performing imaging diagnostic procedures are magnified.

At least one particularly difficult image to obtain is a lateral image of the hip joint after a suspected fracture of the hip. The patient is oriented on his/her back and the unaffected leg is required to be elevated away from the lower leg, with the knee joint bent to approximately a 90° angle (flexion), and the hip joint bent about 90° away from the straight. An imaging sensor is placed beside the affected leg at the hip joint and x-ray source is located inferiorly and laterally relative to the unaffected side, while oriented to image the lower leg hip joint with the imaging equipment pointing in a cephalid and medial direction. A disproportionately large number of suspected hip fracture patients are elderly, and can have difficulty in holding the upper leg at such extreme flexion. Furthermore, often tremendous pain is associated with a hip injury with suspected fracture, as well as with many other conditions which patients are experiencing at a time when imaging procedures are needed.

In the prior art, when obtaining images such as those described above, one option is for the x-ray technician to hold the upper leg in the desired position while the imaging procedure is conducted and the image is acquired, by interaction between the imaging radiation source and the imaging sensor. Often such imaging equipment is a source of x-rays and the sensor is a sensor with an array of x-ray detectors. While modern x-ray equipment and sensors have become highly sensitive to even relatively low amounts of x-ray radiation, a medically significant dose of radiation is still encountered by the patient when using x-ray imaging equipment. When anatomical posture is difficult to achieve, a potential for requiring additional imaging procedures to obtain required images is increased, thus increasing the dose received by the patient. When the x-ray technician needs to hold the upper leg in imaging procedures such as those described above, the x-ray technician also receives a medically significant dose of radiation. Accordingly, a need exists for a support system which can hold a lower extremity of a patient in a desired anatomical posture so that the very best medical imaging procedures can occur, enhancing the overall image quality and quality of patient care, improving outcomes.

While a particular example is provided above with regard to imaging required for suspected hip fractures, many other lower extremity images could be enhanced if a suitable support tool were available to hold lower extremities of the patient in an optimal position and orientation in support of imaging procedures. Furthermore, at least some medical procedures such as orthopedic surgery procedures or other procedures on the lower extremities of a patient, would be facilitated if position and orientation of the lower extremities could be achieved by a support tool, and not require the active and ongoing participation of medical personnel. Such procedures could include surgery on portions of the leg, foot or ankle, and such as during procedures such as debridement, incision and drainage, fixation or other medical procedures.

SUMMARY OF THE INVENTION

With this invention, a support tool (also referred to as a "stand") is provided for leg (or arm) support. While this tool could potentially be mounted to a bed, table or other structure, most preferably it is supported upon the floor, including wheels to assist in mobility thereof. One embodiment of such a support stand is described in detail herein according to a preferred embodiment, which is also disclosed in the included figures. Other embodiments could be provided with various modifications to this example embodiment disclosed herein.

Generally, the stand includes four major parts. First, a lower base which provides a foundation of support for the stand upon the floor. Second, a riser extending up from the base. Third, at least one arm extending from an upper portion of the riser generally laterally to an anatomical support location. Fourth, a cradle carried by the arm which directly provides the support function for a portion of the leg (or arm) of the patient, most typically the calf of the patient between the knee and the ankle.

In this embodiment, the base includes two elongate legs which are parallel and spaced apart from each other a sufficient distance (such as about 24 inches) and with sufficient length (such as about 36 inches) that steady support for elevated portions of the stand is provided. Each of these legs are formed of high strength rigid material, such as steel. If desired, feet can be provided under the legs which directly interact with the floor. Preferably, the legs merely have a horizontal planar under surface which rests upon the floor. If desired, ends of the legs can be angled to be just slightly lower than mid-portions of the leg, so that support of the overall stand is provided through the base primarily at four corners including distal and proximal ends of each leg.

Wheels are rotatably mounted to a crossbar of the base near proximal ends of each leg in this example embodiment. These wheels are preferably positioned so that when the legs are horizontal to the floor, the wheels are up off of the floor and positioned slightly above the legs. However, when the riser is tilted away from a more vertical orientation to a less vertical orientation, or otherwise pivoted about the crossbar, the wheels transition to being at least slightly lower than proximal ends of the legs, and slightly lower than all other portions of the base, so that the entire stand can be carried upon the wheels and rolled about upon the floor. As an alternative, the wheels could always be in contact with the floor and could include some locking mechanism so that the wheels can be locked when desired, such as when the stand is in a desired position for use or is being stored.

As one option, the geometry of the stand can be such that it has a complemental shape relative to a portable x-ray machine or other portable imaging equipment. With such a complementary shape, the stand and imaging tool could be stored together with the various portions thereof nesting at least somewhat together, so that a common single storage space can store both the support tool and the mobile imaging equipment. As a further option, the stand could be provided without wheels and be configured to be carried by the mobile x-ray machine or other imaging equipment with the legs elevated above the floor slightly and the entire stand having its weight carried by the mobile x-ray machine or other mobile imaging equipment, so that portability of the stand is provided through the portability mechanisms associated with the imaging equipment. In such an embodiment, the stand would be decoupled from the imaging equipment and then slid upon the floor or roll on wheels, or otherwise moved to a desired anatomical lower extremity support position during set up of the imaging equipment, such as in a hospital room or other care environment.

A lower end of the riser is structurally supported by the base through any of a variety of different structural elements providing rigid coupling between the lower end of the riser and the legs of the base. In one embodiment, these interconnecting structural members include gussets which connect to the legs somewhat distally from the proximal end of the legs, but then extending upwardly and proximally to upper ends of the gussets, and positioned generally above the wheels and at approximately a midpoint between the wheels, defining one effective location for the lower end of the riser to be fixed relative to the base.

The riser is a rigid structure which extends at least somewhat vertically up from the base to support the arms at an elevated location relative to the base. In one embodiment, this riser is linear in form and extends vertically up from a lower end being adjacent to the base, to a top end preferably slightly above the arms. The riser can have a fixed height or the riser can be height adjustable so that an elevation of the arms above the legs can be adjusted through adjustment of height of the riser. In one embodiment, the riser is formed of a left and right pair of concentric cylindrical objects, including a sleeve and post. The sleeve would have a hollow cylindrical core sized slightly larger than an exterior of the post. The sleeve of the riser could thus telescope up and down relative to the fixed post.

The fixed post would be coupled to the base at the lower end of the riser. The sleeve of the riser would be affixed to the arms. In this way, when the sleeve is translated relative to the post, such a telescoping action will adjust height of the arms relative to the base. In one embodiment, the sleeve and post are similar in length so that a height of the riser can be readily adjusted at least 50% of a height of the riser, and still leave the sleeve and post nested together at least 50%. As one option, holes can be provided in the sleeves and/or posts with spring-loaded pins mounted to a portion of the posts (or to a lock structure) which can be readily grasped by a user. These pins can be aligned with various different holes at different elevations along the sleeves and poles.

A lock tool mounted to the sleeves can carry the pins and have the pins snap into different holes in the sleeves and/or posts. The lock can have a handle, with the handle graspable by a user when the lock is in an unlocked position, and elevation of the sleeves relative to the posts can occur until the arms have a desired height. The lock can then be released, and the pins can register with holes nearby, leaving the arms held securely at a desired elevation above the base. As an alternative, some form of friction clamp could be utilized with locking and unlocking of the sleeves relative to the posts occurring through engagement and disengagement of such a friction clamp.

As further options for elevation of the riser, as one option the riser could be configured to allow for automatic raising and lowering thereof. For instance, the post and sleeve could be replaced with a cylinder and rod, with a piston within the cylinder and with a fluid space within the cylinder and on one side of the piston. The cylinder would be mounted to the base and the rod would be mounted to the arms (or vice versa). Addition of air pressure (or conceivably hydraulic fluid) into the cylinder would cause the piston and arm to move within the cylinder and elevate (or lower) the arms to a desired elevation.

A source of compressed air (or pressurized hydraulic fluid) could be carried upon the stand or otherwise provided, such as on a portion of the base. A controller would interact with valves to add or remove pressurized air (or pressurized fluid) relative to the cylinder for raising and or lowering of the riser in an at least partially automated fashion. Other forms of at least somewhat automated riser function could include chains and/or belts and sprockets and/or pulleys/sheaves interposed between the poles and sleeves of the risers or other elongate elements movable relative to each other, and with some form of drive for the chains etc. to cause elevation and lowering of the arms. Direct gearing of sleeves and poles or similar elements together could also be utilized in a corresponding fashion.

As another option, the riser can be a single rigid elongate structure and the arm configured to be coupled at different heights to the riser. For instance, a junction on a proximal end of the arm can releasably attach at various elevations to the riser. In one form, the riser has teeth on a left side and the arm extends to the right. A bar associated with the junction releasably engages the teeth to allow the arm to be elevated, lowered and affixed to the riser where desired.

An uppermost end of the riser preferably is provided as a handle which can be gripped to assist in moving the support stand. When the support stand is pivoted to have the stand carried upon wheels thereof, the handle can be utilized to help facilitate such pivoting and also to carry the support stand to a desired location while weight of the support system is primarily carried upon the wheels. When the riser is configured as a pair of posts and sleeves parallel to each other, the handle can merely be a rigid structure joined to upper ends of each of the sleeves/post pairs which make up of the overall riser structure.

The arm in this example embodiment is provided extending horizontally away from upper portions of the riser. While the arm could be adjustable in length, in a simplest embodiment it is of fixed length and extends typically no more than the length of the legs of the base, such as about 30 inches, such that the ends of the arms carry loads which are inboard of corners of the base for secure support provided near the distal end of the arm.

In one embodiment the arm could be provided as a single arm, but in other example embodiments two (or more) parallel arms are provided of similar length. Each arm is preferably a rigid structure and is elongate and linear in form. In one embodiment, at least distal portions of the arm (or arms) is formed of radiolucent material so that if portions of the arm are within a field between the imaging equipment and the sensor, the arm will not obscure anatomical details within the resulting image. Furthermore, such non-anatomical structures within the images, having a known location, can act to some extent as reference points for anatomical structures appearing within the images. Typically, some form of a gusset is provided beneath the arm (or arms) and diagonal in form to help support loads bearing upon the arms and the weight of the arms themselves by the riser, and carrying these loads down to the base with a sufficient rigidity and strength that secure holding of extremities of the patient can occur near the ends of the arm.

If desired, some amount of adjustability of the arm can be provided, such as length adjustability or pivoting of the arm either about a vertical axis or about a horizontal axis, to provide further degrees of freedom for upper portions of the support stand. Any such further adjustability would typically be provided near a junction between the arm and the riser.

A cradle is supported upon the distal end of the arm so that the cradle has at least one (and preferably multiple) degree(s) of freedom relative to the arm. These two degrees of freedom can for instance facilitate knee flexion and leg adduction/abduction, while the leg is resting within a trough of the cradle. A pivot mechanism allows for pivoting of the cradle relative to the arm about a substantially vertical axis. A tilt mechanism allows for tilting of the cradle relative to the arm about a horizontal axis aligned with the arm.

The cradle is preferably formed of a radiolucent material so that it is invisible or largely invisible to the imaging modality. In the embodiment disclosed, the cradle is semi-cylindrical in form and generally open on an upper portion thereof. Two ends can be truncated in a tapering fashion, as an option, so the lower portions of the cradle are located further from each other than upper portions of the cradle, defined by opposing parallel edges of the trough shaped cradle. The cradle is generally "concave up" in orientation and acts somewhat as a saddle to provide secure support for a portion of the anatomy of a patient, such as a portion of the leg of the patient between the knee and the ankle. One suitable material for forming the cradle could be carbon fiber. Such a material would also avoid placing significant weight near the distal end of the arm, which could otherwise tend to make the support stand less stable and/or require that the legs be longer (or the base heavier) to stabilize the support stand. Other suitable materials could include fiberglass, or various forms of plastics.

Most preferably, a joint between the cradle and the arm has two degrees of freedom, with a loose configuration where are the two degrees of freedom can be freely adjusted, and a tight configuration where the cradle is frozen relative to the arm in whatever position it is in when the joint is tightened. While the pivot pin could be configured as a form of universal joint to provide both degrees of freedom, two separate adjacent joints could be provided to provide the two different degrees of freedom singularly by each of the two joints, and potentially with a single "tightener" for the entire joint or with separate "tighteners" for each of the two joints, if separate.

OBJECTS OF THE INVENTION

Accordingly, a primary object of the present invention is to provide a support tool which can support a bodily extremity of a patient, such as for an imaging procedure or some other medical procedure.

Another object of the present invention is to provide a support tool which can support a bodily extremity of a patient while the patient is lying in a bed.

Another object of the present invention is to provide a support tool which is highly stable at a location over a bed, and which rests upon a floor under the bed, but is also readily portable.

Another object of the present invention is to provide a support tool which is adjustable in height to accommodate beds of different heights and patients of different sizes and positioning needs for the imaging or medical procedure to be performed on the bodily extremity supported within a cradle of the support tool.

Another object of the present invention is to provide a method for supporting a bodily extremity of a patient in a desired position.

Another object of the present invention is to provide a support tool which can assist in holding a leg of a patient precisely where desired for effective imaging of a hip joint of a patient.

Another object of the present invention is to provide a method and support tool to facilitate high quality medical imaging with a minimum of discomfort for the patient.

Another object of the present invention is to provide a support tool which can roll upon a floor and rest stably upon a floor when at a desired location.

Other further objects of the present invention will become apparent from a careful reading of the included drawing figures, the claims and detailed description of the invention.

BRIEF DESCRIPTION OF THE DRAWINGS

FIG. 3 is a top plan view of that which is shown in FIG. 1.

FIG. 4 is a front elevation view of that which is shown in FIG. 1.

FIG. 5 is a detail of a housing which supports a pivot mechanism for pivoting the cradle and a tilt mechanism for tilting the cradle relative to the arm of a support provided according to this invention.

FIG. 6 is a right side view of that which is shown in FIG. 1.

DESCRIPTION OF THE PREFERRED EMBODIMENT

Figure 1:
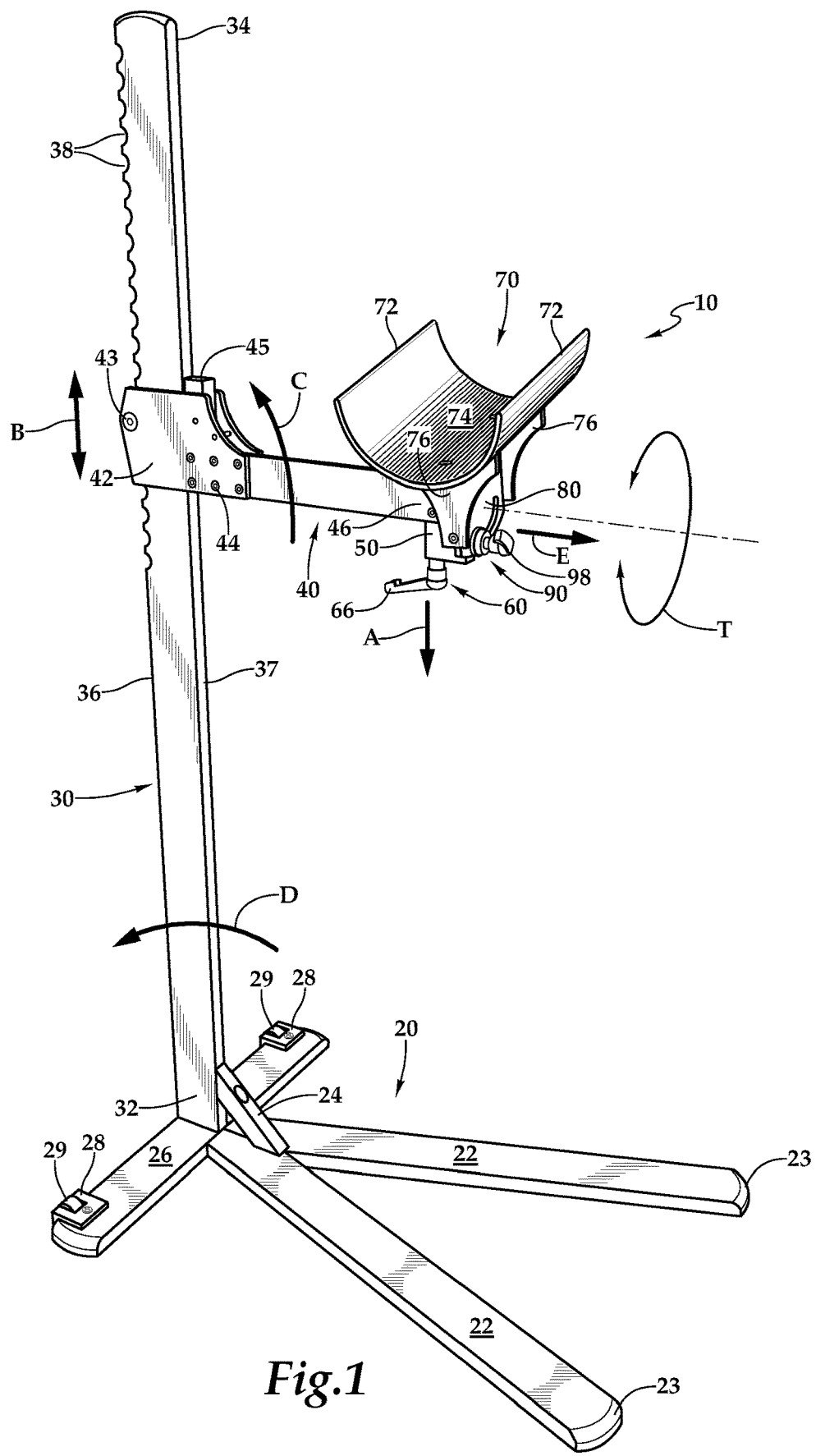
FIG. 1 is a perspective view of a support according to one embodiment of this invention.

Referring to the drawings, wherein like reference numerals represent like parts throughout the various drawing figures, reference numeral 10 is directed to a stand (FIGS. 1 and 2) which acts as a support tool, such as for use in facilitating x-ray imaging of a bodily extremity, such as a leg or an arm of a patient. The stand 10 in this embodiment is readily portable and is especially configured to have a base which fits under a bed and allows for positioning of a leg of a patient while the patient is lying in the bed, such as for obtaining an x-ray of a hip joint, and with a minimum of discomfort for the patient.

Figure 2:
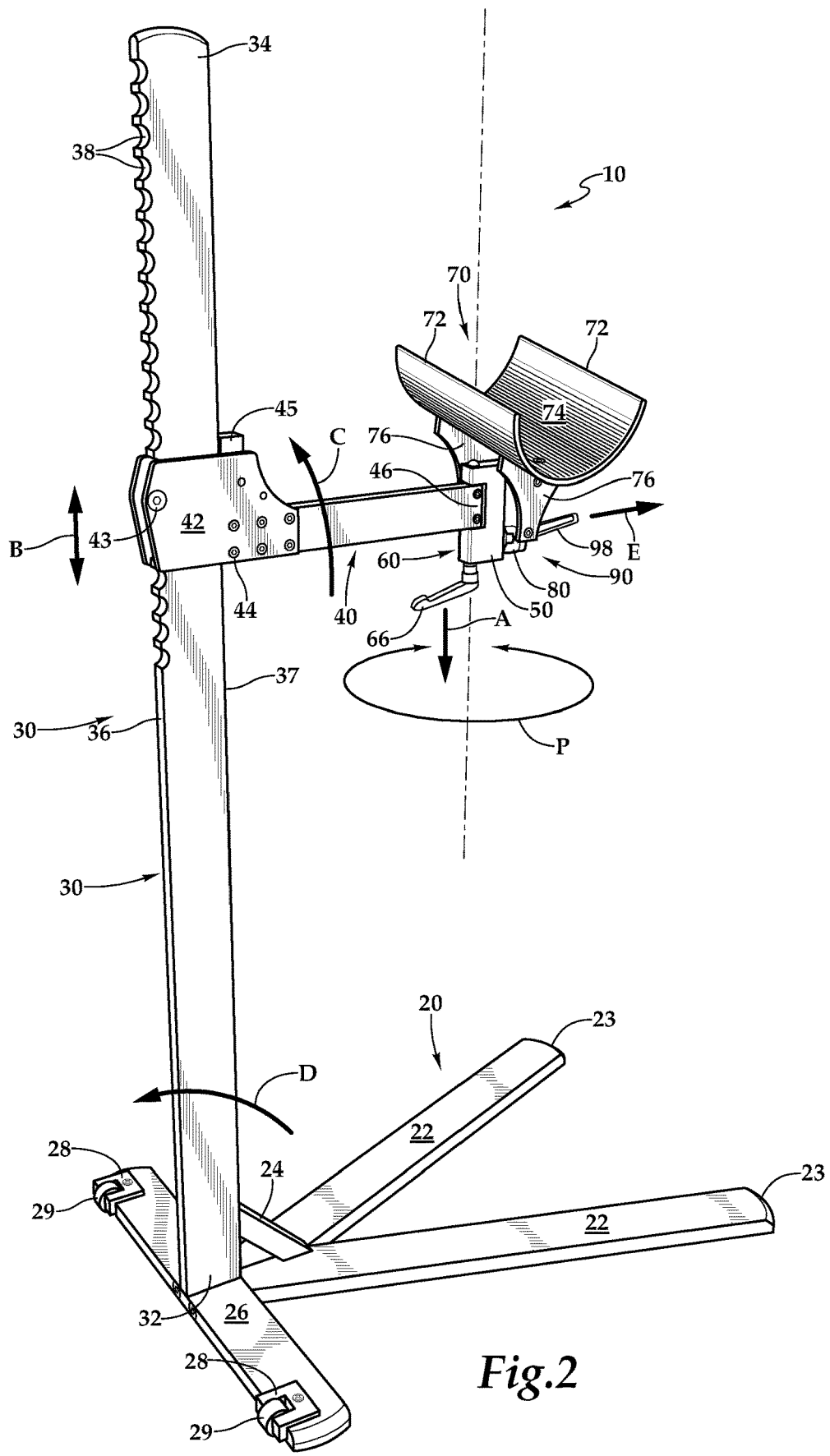
FIG. 2 is a perspective view of that which is shown in FIG. 1, but from a more leftward point of view.

In essence, and with particular reference to FIGS. 1 and 2, basic details of the stand 10 are described, according to this example embodiment. The stand 10 is supported upon an underlying floor through a base 20. A riser 30 extends up from the base, preferably with the riser 30 at a left side of the stand 10, while a center of the base 20 is oriented at a right side of the riser 30. An arm 40 extends laterally from the riser 30 and to a right side of the riser 30, so that the arm 40 is located generally over a center of the base 20. A pivot housing 50 is at a distal end 46 of the arm 40. A cradle 70 is supported by the pivot housing 50 and is configured to hold a bodily extremity of the patient therein, the cradle 70 preferably formed of radiolucent material. A pivot mechanism 60 facilitates pivoting of the cradle 70 relative to the arm 40, about a vertical axis. A tilt plate 80 under the cradle 70 acts with a tilt mechanism 90 to support the cradle 70 at different tilt angles away from horizontal. The cradle 70 is thus supported by the stand 10 in a way which allows the cradle 70 to have an optimal position and orientation for supporting a bodily extremity of a patient during an imaging procedure or medical procedure.

More specifically, and with reference to FIGS. 1-4, details of the base 20 are described according to this example embodiment. The base 20 defines a lowermost portion of the stand 10 and provides for stable operation of the stand 10 when stationary, and also facilitates convenient and easy moving of the stand 10 when the stand 10 is to be moved to a location for use or to a location for storage or other transport.

While the base 20 could have a variety of different configurations, the base 20 in this example embodiment is particularly configured to provide stable support for the stand 10 and especially the arm 40 of the stand 10 when use holding a bodily extremity of a patient. To achieve this, the base 20 preferably has a footprint between lateral sides thereof which resides below the arm 40 and keeps the arm 40 within this footprint. In particular, vertical lines extend up from lateral portions of the base 20 (to a front and a rear) are outboard of the arm 40. In this way, vertical gravity forces associated with objects placed on the cradle 70 coupled to the distal end 46 of the arm 40 are inboard of this footprint of the lateral edges of the base, preventing the stand 10 from toppling over.

The lateral edges of the base 20 are typically defined by legs 22, at least partially. The legs 22 in this embodiment radiate horizontally away from a root 32 of the riser 30 defining a lower end of the riser 30 attached to the base 20. These legs 22 are preferably in the form of a pair of legs 22 each extending to a tip 23, and with the legs 22 being similar in size, shape and length, extending mostly in a rightward direction away from the root 32 of the riser 30, but with one of the legs 22 extending slightly forwardly and the other leg 22 extending slightly rearwardly. Most preferably, the tips 23 are spaced sufficiently far from a root 32 of the riser 30 that they extend beyond the cradle 70. Stated alternatively, preferably the legs 22 are longer than the arm 40 so that the cradle 70 is closer to the riser 30 than the tips 23 of the legs 22.

The base 20 also preferably includes a crossbar 26 extending forwardly and rearwardly in line with the riser 30, with the crossbar 26 remaining in a horizontal plane along with the legs 22. The crossbar 26 adds further lateral stability to the base 20. A gusset 24 preferably extends diagonally between the riser 30 and portions of the base 20, such as between the legs 22. The gusset 24 improves a strength with which the root 32 of the riser 30 is attached to the base 20.

Wheel supports 28 are preferably mounted near ends of the crossbar 26. Each wheel support 28 rotatably supports at least one wheel 29 thereon. The wheel supports 28 and wheels 29 are sized and positioned so that when the legs 22 and crossbar 26 are resting on a floor or other horizontal flat surface, the wheels 29 are preferably not touching this floor or other underlying horizontal surface, but rather are elevated slightly. In this way, the base 20 does not roll about on the wheels 29 when the base 20 is oriented within a horizontal plane, with the riser 30 extending vertically upward therefrom, in its use configuration. However, when the riser 30 is tilted out of this vertical orientation (along arrow D of FIGS. 1, 2 and 4) sufficient tilting will cause the wheels 29 to come into contract with the floor or other underlying surface. Further tilting along arrow D will cause the crossbar 26 and other portions of the base 20 to be entirely off of the floor so that only the wheels 29 are in contact with the floor. A user can conveniently hold upper portions of the riser 30 and can then easily move the stand 10 while it is rolling upon the wheels 29.

The stand 10 can be rolled to a location where it is to be used, and then tilted to have the riser 30 extending vertically and with the base 20 firmly upon the floor and the wheels 29 pivoted up out of contact with the floor. When the stand 10 is being moved in this fashion, it can be moved manually by user, such as when the user is grasping upper portions for the riser 30. As another option, the riser 30 or other portions of the stand 10 can be attached to a cart or other wheeled object. For instance, in a hospital or other clinical setting it is known to have a portable x-ray machine or other portable imaging devices or carts utilizable with such imaging devices. The stand 10 can be configured to attach to such a cart, so that a user of the imaging system and cart associated therewith can also conveniently have the stand 10 carried along, much in the way that a trailer is carried by a prime mover vehicle, as an option. A strap or hitch can be mounted to such a cart or portable imaging device or can be mounted to the riser 30 or other portions of the stand 10 to facilitate secure but temporary interconnection therebetween. In this way, a single user can move the portable imaging system and/or any cart associated therewith and simultaneously also move the stand 10 to a location where an imaging procedure is to occur. Similarly, medical procedures can be facilitated by having an appropriate cart or other mobile conveyance utilizable with such a medical procedure carry the stand 10 by attachment thereto, while the stand 10 is resting upon its wheels 29, so the stand 10 is available at the location where the medical procedure is to be performed.

With a particular reference to FIGS. 1-4, details of the riser 30 are described according to this example embodiment. The riser 30 is an elongate rigid structure formed of a material and with dimensions which give the riser 30 sufficient strength to carry loads associated with a bodily extremity resting upon the cradle 70, and also carrying weight of the cradle 70 itself and the arm 40 and pivot housing 50. In this embodiment, the riser 30 extends from the root 32 up to a top 34, with a distance between the root 32 and top 34 generally defining a height of the overall stand 10. Typically this height is approximately four or five feet.

The riser 30 includes a left side 36 and a right side 37 opposite the left side 36. A series of teeth 38 are provided on the left side 36. The right side 37 defines a side of the riser 30 closest to the arm 40 and cradle 70. The teeth 38 assist in adjustably holding the arm 40 at different elevation horizontally extending positions from the riser 30, as described in detail below according to this example embodiment. It is recognized that systems for controlling height of the riser 30 and/or the arm 40 relative to the base 20 could differ from those disclosed below, either using locking pins/supports similar to those used to control pivot and/or tilt of the cradle 70 or systems such as those described in the Summary of the Invention above.

With continued reference to FIGS. 1-4, details of the arm 40 are described, according to this example embodiment. The arm 40 is a rigid elongate structure which is preferably shorter than the legs 22 but sufficiently long to reach across a bed with portions of the base 20 beneath the bed, and reaching to a location where a bodily extremity of a patient is located, such as an arm or leg of the patient. The arm 40 is preferably long enough that the cradle 70 can be positioned to support either a leg or arm closest to a side of the bed where the riser 30 of the stand 10 is located or an arm or leg of the patient opposite a side of the bed where the riser of the stand 10 is located. Thus, the arm 40 is preferably approximately ⅔ of a length of a width of a typical hospital bed, such as about 2½ to 3 feet long.

A junction 42 is provided at a left end of the arm 40. This junction 42 is preferably in the form of a pair of plates which are parallel to each other and spaced apart by a distance similar to a thickness of the riser 30 between front and rear surfaces thereof. The junction 42 thus has a gap between the two plates through which the riser 30 is adjustably positionable. A bar 43 is located on an upper left side of the junction 42. This bar 43 is sized to reside within gaps 38 between teeth on the riser 30. The arm 40 has a rest 44 between the two plates formed in the junction 42 and on a lower right side of the riser 30. A horizontal spacing between the rest 44 the bar 43 is preferably similar to a width of the riser 30 between the left side 36 and right side 37 when measuring to an inside of the gaps 38 between teeth. In this way, the junction 42 and associated arm 40 cannot move vertically downward when the bar 43 is residing within gaps 38 between teeth. Rather, the bar 43 is captured within one of the gaps 38, preventing the junction 42 and associated arm 40 from moving downward.

However, when the arm 40 is pivoted (along arrow C of FIGS. 1, 2 and 4) spacing between the bar 43 at an upper left corner of the junction 42 and the rest 44 at the lower right corner of the junction 42 is increased in the horizontal direction. This increase is sufficient to move the bar 43 out of one of the gaps 38 between the teeth and to allow for vertical repositioning of the arm 40 (along arrow B of FIGS. 1, 2 and 4). When the arm 40 is returned to its horizontal orientation, the bar 43 engages in a gap 38 between teeth in the riser 30 for again securely holding the arm 40 horizontally extending away from the riser 30. Because the center of mass of the arm 40 is spaced away from the junction 42, and because downward gravity force is not on the arm 40 tending to cause rotation of the arm 40 further (opposite the direction of arrow C of FIGS. 1, 2 and 4), the arm 40 remains fixed in position by gravity forces alone. As weight is added to the arm 40, the arm 40 holds even more securely to the riser 30. To prevent inadvertent jostling of the arm 40 to cause the junction 42 to disengage the riser 30, a stop 45 can be provided at an upper right portion of the junction 42 between the two plates. This stop 45 can be placed into this position and further prevents rotation of the arm 40 (along arrow C of FIGS. 1 and 2) unless the stop 45 is first moved at least partially out of position to facilitate upward rotation of the arm 40 (along arrow C) and height adjustment (along arrow B).

The arm 40 preferably extends linearly away from the junction 42 to a distal end 46. The distal end 46 is pivotably supported to a pivot housing 50 to which the cradle 70 is attached. The distal end 46 of the arm 40 resides within a notch 56 formed in the side of the pivot housing 50 facing the arm 40 and riser 30. The arm 40 has a spring loaded pin 48 extending vertically upward from the distal end 46 of the arm 40. This pin 48 resides within a recess 47 in the distal end 46 of the arm 40 and is actuated by spring 49 to be biased toward a position elevated up out of an upper surface of the distal end 46 of the arm 40, and up into a bore 53 in an upper portion of the pivot housing 50. Once this pin 48 snaps into the bar 53, the pivot housing 50 can pivot about this pin 48 (about a vertical axis and along arrow P (see FIGS. 2 and 3) to facilitate pivoting of the cradle 70 relative to the arm 40.

The pivot housing 50 has generally a C-shaped form with an upper end 52 above the distal end 46 of the arm 40 and a lower end 54 below the distal end 46 of the arm 40, and with the notch 56 between the upper end 52 and lower end 54. A cavity 55 is provided in the lower end 54, which cavity 55 supports at least portions of a pivot mechanism 60 to allow or restrain pivot motion about a substantially vertical axis (along arrow P of FIGS. 2 and 3).

The pivot mechanism 60 is provided to facilitate pivoting (along arrow P of FIGS. 2 and 3) about a vertical axis, and to also allow for locking of the cradle 70 in fixed orientation relative to the arm 40 when the cradle 70 is positioned and oriented as desired. In particular, the pivot mechanism 60 includes a clutch plate 62 at an upper end of a shaft 63 and with a spring 64 bearing on a lower surface of this clutch plate 62. The shaft 63 extends down through the cavity 55 which exits the lower end 54 of the pivot housing 50, and with a handle 66 mounted to a lower end of the shaft 63. The handle 66 can be moved downwardly (along arrow A of FIGS. 1, 2, 4 and 5) which causes the clutch plate 62 to move off of a base 41 on the lower surface of the arm 40 which resides within an upper portion of the cavity 55 to keep the arm 50 generally aligned relative to the pivot housing 50. Locking teeth or ribs on the base 41 and/or the clutch plate 62 can enhance this locking effect. When the handle 66 is released, the spring 64 apply sufficient frictional force between the clutch plate 62 and bus 41 that the arm 40 is prevented from rotating relative to the pivot housing 50. With the cradle 70 affixed to the pivot housing 50, the cradle 70 is fixed relative to the arm 40 through action of the spring 64 on the clutch plate 62 when the handle 66 is not manipulated. However, when the handle 66 is moved downward (along arrow A of FIGS. 1, 2, 4 and 5) the clutch plate 62 is disengaged from the base 41, and can pivot freely (about arrow P of FIGS. 2 and 3) for pivoting orientation of the cradle 70 relative to the arm 40. In this example embodiment, the cradle 70 can also be tilted about a horizontal axis generally aligned with the arm 43 through utilization of a tilt plate 80 and tilt mechanism 90, described in detail below.

With continuing reference to FIGS. 1-4, details of the cradle 70 are described, according to this example embodiment. The cradle 70 is a rigid structure which holds a bodily extremity therein, such as during a medical procedure or imaging procedure. This cradle 70 is preferably an open sided trough in which an elongate bodily extremity can be placed and supported. The cradle 70 includes opposing edges 72 which point upwardly and define an uppermost portion of the cradle 70. A saddle 74 is located between the opposing edges 72 and has a concave up orientation.

In one embodiment, this saddle 74 causes the cradle 70 to be semi-cylindrical in form, defining half of a cylinder. In other embodiments, the cradle 70 could be a portion of some other shape akin to a semi-cylinder, but not exactly a semi-cylinder, such as a portion of a cylinder with an oval cross-section or ellipsoidal cross-section. The cradle 70 could be half of a cylinder or some portion slightly greater or less than half of a cylinder. While the opposing edges 72 of the cradle 70 are preferably horizontal and coplanar with each other, it is conceivable that the two opposing edges 72 could have different elevations, shapes or orientations. A strap can be provided as well to hold a bodily extremity still in the cradle 70.

The cradle 70 is preferably formed of radiolucent material. For instance, the cradle 70 can be formed of a plastic or other polymeric hydrocarbon material which is generally invisible to x-rays and other imaging and/or treatment radiation. A variety of other at least partially radiolucent materials could alternatively be utilized. As another option, the cradle 70 could be formed of material which is sufficiently radiopaque that at least an outline of the cradle 70 can be seen, or radiopaque markers attached to the cradle 70, such as to provide reference points within images obtained utilizing imaging equipment.

The cradle 70 preferably attaches to the pivot housing 50 through the tilt plate 80. The tilt plate 80 can be oriented within a vertical plane, with a plane in which the tilt plate 80 is oriented aligned with a central axis of the cradle 70. An upper edge 86 of the tilt plate 80 can run along an underside of the cradle 70 at a lowermost portion of the cradle 70, midway between the opposing edges 72 of the cradle 70. The tilt plate 80 extends down to a lower edge 84 opposite the upper edge 86. An arcuate slot 88 is located near the lower edge 84 and assists with the tilt mechanism 90. Lateral edges 82 of the tilt plate 80 are preferably adjacent to a pair of yokes 76 which are shaped to underlie and support front and rear portions of the cradle 70.

The tilt mechanism 90 is provided by mounting the tilt plate 80 to the pivot housing 50 through a tilt pin 92. This tilt pin 92 has a central axis thereof aligned with a radius of curvature of the arcuate slot 88 in the tilt plate 80 and extending generally horizontally. The lower end 54 of the pivot housing 50 includes a chamber 93 therein which is open at a right side of the pivot housing 50. The chamber 93 supports a shaft 96 along with a spring 95 and brake 94, and handle 98. The spring 94 is a tension spring which is preloaded somewhat, passing the brake 94 and handle 98 to abut portions of the tilt plate 80 adjacent to the arcuate slot 88. The shaft 96 maintains alignment of the brake 94 with the spring 95 and handle 98.

The handle 98 can be grasped and translated horizontally (along arrow E of FIGS. 1, 2, 4 and 5) to cause the brake 94 to move away from the tilt plate 80, and in which orientation the tilt plate 80 can be tilted (along arrow T of FIGS. 1 and 6) by having the arcuate slot 88 move relative to the shaft 96 of the tilt mechanism 90. When the handle 98 is released, the brake 94 again engages the tilt plate 80 and the associated cradle 70 is held in the position in which the cradle 70 is oriented when the handle 98 is released.

In use and operation, and with continuing reference to FIGS. 1-6, users such as a medical imaging specialist will wheel (or otherwise slide or carry) the stand 10 to a location where images are to be gathered, such as at a bedside of a patient. The base 20 and especially the legs 22 of the base 20 are inserted under the bed where the patient is lying. If a leg of the patient needs to be lifted to allow for a desired image to be acquired, the arm 40 of the stand 10 is maneuvered along with the rest of the stand 10 to place the cradle 70 near where the leg of the patient is to be supported.

Next, the technician determines whether the cradle 70 needs to be pivoted about a vertical axis or tilted about a horizontal axis. If pivoting is called for, they handle 66 is pulled downward (along arrow A), unlocking the cradle 70 relative to the pivot housing 50, and the cradle 70 can be pivoted to a desired orientation (along arrow P). When the desired orientation is achieved, the handle 66 is released and spring action causes the cradle 70 to maintain the position in which it is left. Next, if tilting of the cradle 70 is desired, the user pulls on the handle 98, allowing the cradle 70 to be tilted freely (along arrow T of FIGS. 1 and 6). Once the cradle 70 has been tilted to the desired orientation, the handle 98 is released and the cradle 70 maintains this tilt orientation. Such fine tuning of pivoting and tilt of the cradle 70 can either occur before the leg of the patient has been placed on the cradle 70 or after the leg of the patient has been placed upon the cradle 70. Appropriate medical images can then be obtained.

A similar procedure can be adapted for supporting an arm of a patient, either while the patient is lying in a bed or sitting in a chair (or standing). Similarly, various medical procedures can be conducted on an extremity of the patient while the patient's extremity is resting upon the cradle 70, utilizing a similar procedure to that described above. Finally, the patient's bodily extremities are removed from the cradle 70 and the stand 10 cant be moved to a storage location or to a new location for reuse with another procedure.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. For instance, the tilt mechanism 90 and the pivot mechanism 60 could be configured to use handle rotation between a locked and an unlocked position rather than handle pulling (or pushing). The handles could be alternatively configured as buttons or having other shapes. When embodiments are referred to as "exemplary" or "preferred" this term is meant to indicate one example of the invention, and does not exclude other possible embodiments. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A lower extremity support tool, comprising in combination:
   a base;
   a riser extending up from said base and coupled to said base, at least indirectly;
   at least one arm extending laterally from said riser on a portion of said riser above said base;
   a cradle carried by said at least one arm on a portion of said arm spaced from said riser;
   wherein said cradle is formed of radiolucent material;
   wherein said base includes at least two wheels thereon;
   wherein said cradle is pivotable about a vertical axis;
   wherein said cradle includes opposing edges which are oriented within a common substantially horizontal plane in a first orientation, and which cradle is tiltable into a second orientation, to cause said opposing edges to tilt away from said substantially horizontal plane; and
   wherein said base includes an underlying surface, with said at least two wheels elevated above said underlying surface when said underlying surface is oriented horizontally upon a planar horizontal floor.

2. The tool of claim 1 wherein said cradle is semi-cylindrical in form with an open upper portion and with a central axis of said cradle extending closer to horizontal than to vertical.

3. The tool of claim 1 wherein said riser is adjustable in height to adjust a position of said arm relative to said base.

4. The tool of claim 3 wherein said riser includes teeth on a left side thereof with said arm extending from a right side thereof, said arm including a bar on said left side of said riser which engages with one of said teeth when said arm is horizontal, and is released from said teeth when said arm is raised above horizontal.

5. The tool of claim 1 wherein said base includes at least two wheels thereon.

6. The tool of claim 5 wherein said base includes at least two legs, said wheels located no lower than said legs when said legs are oriented horizontally and resting upon an underlying surface.

7. The tool of claim 1 wherein said base includes a pair of horizontal legs with proximal ends closer to said riser and distal ends further from said riser, said legs oriented closer to parallel in relative orientation than to perpendicular.

8. The tool of claim 1 wherein said base includes at least two legs, and wherein said legs extend further from said riser than said arm.

9. The tool of claim 1 wherein said cradle is pivotable about a vertical axis.

10. The tool of claim 9 wherein said cradle is pivotable relative to said arm.

11. The tool of claim 1 wherein said cradle includes opposing edges which are oriented within a common substantially horizontal plane in a first orientation, and which cradle is tiltable into a second orientation, to cause said opposing edges to tilt away from said substantially horizontal plane.

12. The tool of claim 11 wherein said cradle is tiltable relative to said arm.

13. A bodily extremity medical support, comprising in combination:
  a base;
  a riser extending up from said base to a top;
  at least one leg extending laterally from said riser to a tip, said at least one leg coupled to said riser, at least indirectly;
  at least one arm extending laterally from said riser on a portion of said riser above said base and above said at least one leg;
  said at least one arm located inboard of lateral edges of a footprint of said at least one leg;
  a cradle carried by said at least one arm on a portion of said arm spaced from said riser;
  wherein said cradle is formed of radiolucent material;
  wherein said base includes at least two wheels thereon;
  wherein said cradle is pivotable about a vertical axis;
  wherein said cradle includes opposing edges which are oriented within a common substantially horizontal plane in a first orientation, and which cradle is tiltable into a second orientation, to cause said opposing edges to tilt away from said substantially horizontal plane; and
  wherein said base includes an underlying surface, with said at least two wheels elevated above said underlying surface when said underlying surface is oriented horizontally upon a planar horizontal floor.

14. The support of claim 13 wherein said cradle is semi-cylindrical in form with an open upper portion and with a central axis of said cradle extending closer to horizontal than to vertical.

15. The support of claim 13 wherein said arm is adjustable in height relative to said riser, to adjust a position of said cradle relative to said base.

16. The support of claim 15 wherein said riser includes teeth on a left side thereof with said arm extending from a right side thereof, said arm including a bar on said left side of said riser which engages with one of said teeth when said arm is horizontal, and is released from said teeth when said arm is raised above horizontal.

17. The support of claim 13 wherein said base includes a pair of horizontal legs with proximal ends closer to said riser and distal ends further from said riser, said legs oriented closer to parallel in relative orientation than to perpendicular.

18. The support of claim 13 wherein said legs extend further from said riser than said arm.

19. A lower extremity support tool, comprising in combination:
  a base;
  a riser extending up from said base and coupled to said base, at least indirectly;
  at least one arm extending laterally from said riser on a portion of said riser above said base;
  a cradle carried by said at least one arm on a portion of said arm spaced from said riser;
  wherein said base includes at least two wheels thereon;
  wherein said cradle is pivotable about a vertical axis;
  wherein said cradle includes opposing edges which are oriented within a common substantially horizontal plane in a first orientation, and which cradle is tiltable into a second orientation, to cause said opposing edges to tilt away from said substantially horizontal plane; and
  wherein said base includes an underlying surface, with said at least two wheels elevated above said underlying surface when said underlying surface is oriented horizontally upon a planar horizontal floor.

* * * * *